United States Patent [19]

Hill et al.

[11] Patent Number: 5,434,318

[45] Date of Patent: Jul. 18, 1995

[54] REACTIVATION OR REGENERATION OF COBALT PREFORMER CATALYST FOR OXO PROCESS

[75] Inventors: Ronald R. Hill; Patricia B. Roussel, both of Baton Rouge, La.

[73] Assignee: Exxon Chemical Patents Inc., Wilmington, Del.

[21] Appl. No.: 217,298

[22] Filed: Mar. 23, 1994

[51] Int. Cl.6 .................... C07C 27/20; C07C 29/141; C07C 31/125
[52] U.S. Cl. ...................................... 568/882; 502/28; 568/451; 568/883
[58] Field of Search .................. 568/883, 882, 451

[56] References Cited

U.S. PATENT DOCUMENTS

| | | | |
|---|---|---|---|
| 3,451,943 | 6/1969 | Ruscilli | 518/883 |
| 3,463,741 | 8/1969 | Russell | 568/883 |
| 3,725,534 | 4/1973 | Reisch | 423/417 |
| 3,855,396 | 12/1974 | Kniese et al. | 423/417 |
| 3,929,898 | 12/1975 | Nienburg et al. | 260/604 HF |
| 4,255,279 | 3/1981 | Spohn et al. | 252/413 |
| 4,404,119 | 9/1983 | Lagace et al. | 252/413 |
| 4,625,067 | 11/1986 | Hanin | 568/451 |
| 5,091,599 | 2/1992 | De Munck et al. | 568/882 |
| 5,237,105 | 8/1993 | Summerlin | 568/451 |
| 5,321,168 | 6/1994 | Roussel et al. | 568/882 |

*Primary Examiner*—Joseph E. Evans
*Attorney, Agent, or Firm*—J. J. Mahon; R. D. Jordan

[57] ABSTRACT

Noble metal or other preformer catalysts used to convert cobalt salts to hydrido cobalt carbonyl for use in the oxonation of olefins are reactivated or regenerated by treatment with a mixture of an aqueous organic acid solution and an alcohol at a temperature of about 120° C. to 170° C. and a pressure of about 13.78 MPa to 31.00 MPa for about 2 to 50 hours.

8 Claims, 3 Drawing Sheets

REACTIVATION OR REGENERATION OF COBALT PREFORMER CATALYST FOR OXO PROCESS

This invention relates to the oxo process for preparing oxo alcohols by the hydroformylation of olefins. More particularly, this invention relates to a unique method for reactivating or regenerating the preformer catalyst which is used to effect the conversion of cobalt salts to the active cobalt species in the cobalt catalyzed hydroformylation of the olefins.

BACKGROUND OF THE INVENTION

The oxo process is the commercial application of the hydroformylation reaction for making higher alcohols and aldehydes from olefins. In the cobalt oxo process, an olefin reacts with carbon monoxide and hydrogen (i.e., syn gas) at elevated temperatures in the presence of a cobalt carbonyl catalyst to produce a hydroformylation reaction product which is subsequently decobalted or demetalled to produce a crude product mixture of aldehydes, alcohols, acetals, formates, unreacted olefins and secondary products. Subsequent hydrogenation steps provide the desired finished alcohol products commonly referred to as oxo alcohols (i.e., alcohols produced by an oxonation reaction).

One aspect of the overall cobalt oxo process involves the preparation of the active cobalt catalyst species which is hydrido cobalt carbonyl ($HCo(CO)_4$). Commercial oxo processes employ a preforming step in which this active cobalt catalyst species is prepared using a noble metal preforming catalyst which is contacted with a cobalt salt, e.g., cobalt formate, to provide the desired $HCo(CO)_4$ species.

This preforming step is disclosed, for example, in U.S. Pat. No. 4,404,119, which issued Sep. 13, 1983, to Lagace et al. and in U.S. Pat. No. 4,255,279, which issued Mar. 10, 1981, to Spohn et al.

The present inventors have developed an improvement in the process for preparing oxo alcohols by the cobalt catalyzed hydroformylation of $C_2$ to $C_{17}$ linear or branched monoolefins with subsequent hydrogenation of the hydroformylation reaction product which has been disclosed in co-pending U.S. patent application, Ser. No 08/122,859, filed on Sep. 16, 1993 now U.S. Pat. No. 5,321,168. In this co-pending application the aqueous solutions of cobalt salts have been converted to active hydrido cobalt carbonyl species in a preformer reactor, the preformer containing (i) preformer metal catalyst of Group IB or VIII of the Periodic Table or (ii) a preformer non-metallic catalyst selected from the group consisting of activated carbon, ion exchange resins, silica alumina and zeolites. The preformer catalyst was reactivated according to co-pending U.S. patent application, Ser. No. 08/122,859 by treating it at a temperature of about 120° C. to 170° C. and at a pressure of about 13.78 MPa (2,000 psig) to 31.00 MPa (4,500 psig) and preferably about 20.67 MPa (3,000 psig), with water or with a mixture of water and hydrogen or a mixture of water and syn gas for a period of about 2 to 50 hours, whereby the conversion of the cobalt salts to hydrido cobalt carbonyl is improved when such salts are contacted with the treated preformer catalyst.

However, the reactivation process according to co-pending U.S. patent application, Ser. No. 08/122,859, requires that the preformer solvent or organic feed stream to the preformer reactor be shutoff in order for the catalyst to be treated. This is both time consuming and inefficient.

The present invention does not require shutting off the preformer solvent or organic feed stream during reactivation of the preformer catalyst, but makes use of a readily available preformer solvent in the reactivation step. The preformer solvent (e.g., hexyl alcohol) also allows for the dissolution of organic foulants contained within the pores of the catalyst, thus making it easier for water to enter each pore. It is desirable to have water in the pores during reaction since the $Co^{2+}$ reactant material is in the water phase. The aqueous formic acid solution allows for the dissolution of any deposited cobalt compounds that may deactivate or foul active catalytic sites.

SUMMARY OF THE INVENTION

The present invention reactivates the preformer catalyst by treating it at a temperature of about 120° C. to 170° C. and at a pressure of about 13.78 MPa (2,000 psig) to 31.00 MPa (4,500 psig) with a mixture of preformer solvent (e.g., hexyl alcohol) and an aqueous organic acid solution for a period of about 2 to 50 hours, whereby the conversion of the cobalt salts to hydrido cobalt carbonyl is improved when such salts are contacted with the treated preformer catalyst.

The relative amounts of the aqueous organic acid solution and preformer solvent (e.g., hexyl alcohol) is about 3 to 12 moles of aqueous organic acid solution per mole of preformer solvent with the preferred ratio being about 6 to 8 moles of aqueous organic acid solution per mole of preformer solvent.

DESCRIPTION OF THE PREFERRED EMBODIMENTS

Figure 1:
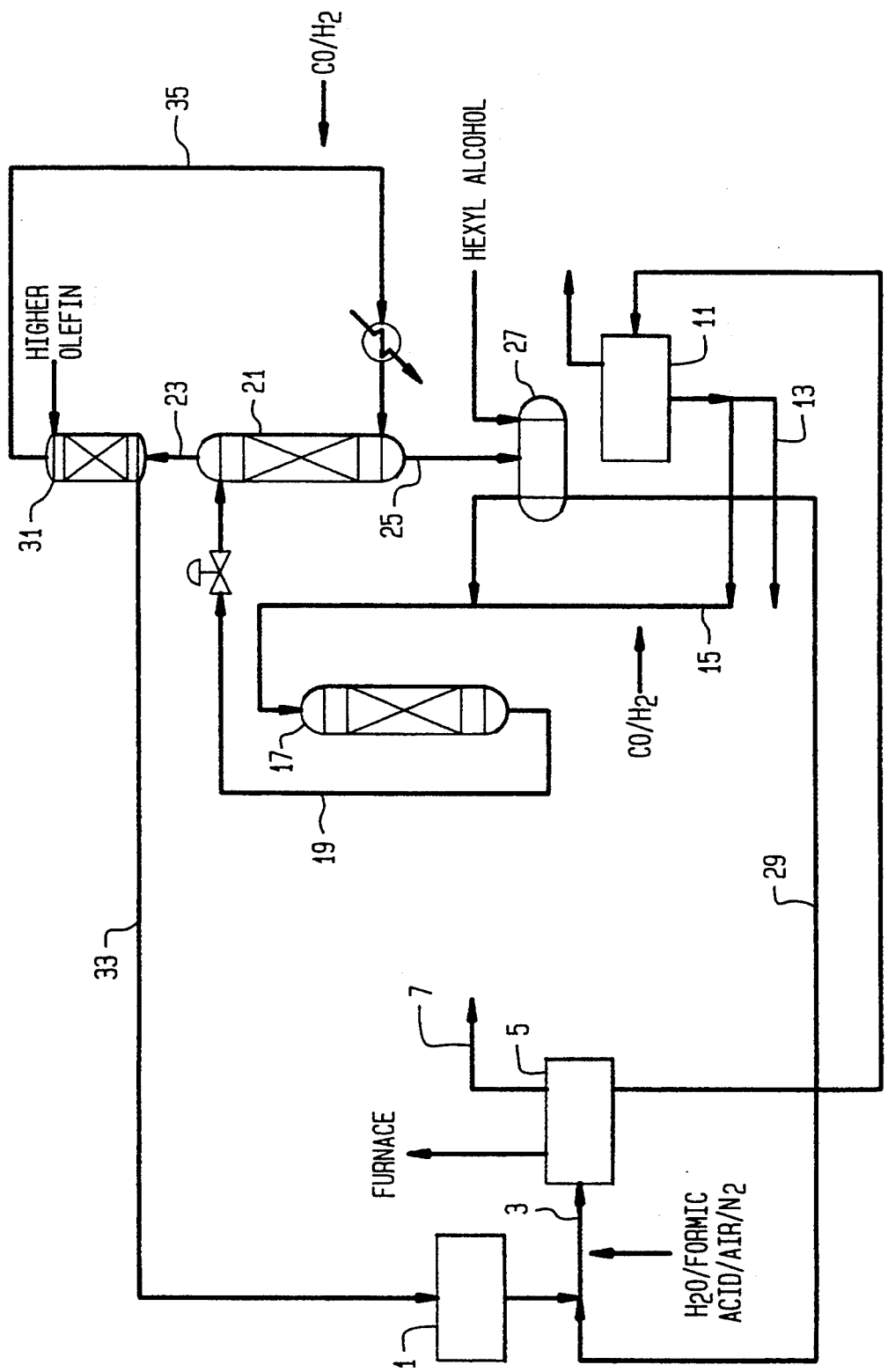
FIG. 1 illustrates an oxo process including a method for removing cobalt values wherein an acid-air cobalt demetalling step is disposed upstream of the stripping step in a Cobalt Flash process.

The present invention is preferably employed in an oxo process in which the olefin is preferably a mixture of linear and branched $C_2$ to $C_{17}$ monoolefins, the hydroformylation typically being carried out at a pressure of 15 to 30 MPa and a temperature of about 120° C. to 190° C. Cobalt is present as hydrido cobalt carbonyl in a concentration of from about 0.05 to 3.0 wt % calculated as metallic cobalt based on olefin feedstock. The synthesis gas (hydrogen and carbon monoxide) typically has a $H_2:CO$ volume ratio in the range of 0.9:1 to 1.5:1, preferably about 1:1.

Particularly preferred preformer catalysts comprise Group IB and VIII metals such as palladium, platinum or gold. Such catalysts may be supported or unsupported using supports such as silica, alumina, zeolites or activated carbon and other carbonaceous support material. The preferred preformer catalyst for use in the invention is about 0.1 to 5 wt %. e.g., 2 wt. % palladium supported on activated carbon.

While the process of this invention is especially useful for the reactivation or regeneration of a noble metal catalyst, such as Pd on activated carbon, it is also applicable to the reactivation or regeneration of preformer catalysts comprising activated carbons, ion exchange resins, silica alumina and zeolites. Suitable zeolites are those having pore diameters of 4 to 12 angstroms. Suitable ion exchange resins are those which contain primary, secondary or tertiary amino groups and are based on polystyrene such as "Amberlite IR45" and Dowex 4". Such catalyst are disclosed in U.S. Pat. No. 3,855,396, issued Dec. 17, 1974, to Kniese et al. and U.S. Pat. No. 3,929,898, issued Dec. 30, 1975, to Nienburg et al.

The preforming reaction is illustrated by the following equations (1) and (2) in which cobalt formate is the illustrative salt undergoing conversion to $HCo(CO)_4$ and Pd is the illustrative preformer catalyst:

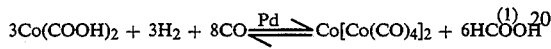

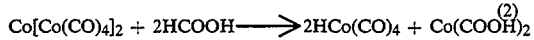

In equation (2) above, the hydrido cobalt carbonyl ($HCo(CO)_4$) is liberated from $Co[Co(CO)_4]$ by the formic acid which is present as a by-product of the hydroformylation process and also as a result of the preforming reaction shown in equation (1) above.

In the operation of the oxo process the preformer treats an aqueous feed containing cobalt salt which is obtained from an acid/air demetalling step, such as is disclosed in U.S. Pat. No. 5,237,105, issued Aug. 17, 1993, to Summerlin, or from the Cobalt Flash stripper bottom, followed by concentration in an evaporator or a flash unit.

The aqueous phase containing the cobalt salts is co-processed over the catalyst with an appropriate organic phase such as an alcohol or mixture of aldehyde/alcohol/hydrocarbon (i.e., crude oxo product). The organic phase is present to minimize cobalt deposition on the active catalyst surface. Hydrido cobalt carbonyl has low solubility in water, but high solubility in organic materials such as mentioned above. In this two liquid phase process, the product carbonyl is continuously extracted into the organic phase. This effectively drives the reaction to higher levels of conversion while minimizing deposition of cobalt on the catalyst.

Once hydrido cobalt carbonyl is extracted into the organic phase, it can form dicobalt octacarbonyl by the following reversible reaction:

The dicobalt octacarbonyl can also dissociate in the presence of an alcohol as indicated below:

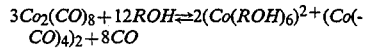

Dicobalt octacarbonyl can also disproportionate with water according to the following reaction:

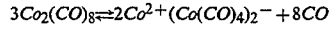

The reactivation or regeneration procedure of this invention may be conducted over a temperature range of about 120° C. to 170° C., preferably at about 150° C. to 160° C., and a pressure of 13.78 MPa to 31.00 MPa (2,000 to 4,500 psig), preferably at about 20.67 MPa to 27.56 MPa (3,000 to 4,000 psig). The catalyst is preferably treated with a high pressure wash, advantageously conducted using a mixture of the preformer solvent (e.g., hexyl alcohol) and an aqueous organic acid solution. The aqueous organic acid solution should be cobalt free and may contain very minor amounts, e.g., about 0.5 to 5.0 wt %, of free organic acid. The treatment should be conducted for a period of about 2 to 50 hours until the catalyst pores become saturated with water.

The organic acid is preferably selected from the group consisting of: formic acid, acetic acid, propionic acid, and other acids having a boiling point approximately the same as water.

The preformer solvent is preferably hexyl alcohol or other light alcohol such as heptyl alcohol, octyl alcohol, butanol or propanol. Although most light alcohols may be suitable for dissolution of organic foulants disposed within the pores of the preformer catalyst, it has been discovered that preformer solvents such as hexyl alcohol may be continuously fed to the preformer reactor via settling drum 27. This avoids the need to shut down the preformer solvent feed during reactivation of the preformer catalyst.

Water treatment will be employed in an amount corresponding to 1.0 to 4.0 LHSV (liquid hourly space velocity), where LHSV is volume feed/hour/volume catalyst. The rate of gas treatment will range from about 0 to 400 GHSV (gas hourly space velocity), preferably about 50 to 200 GHSV, where GHSV is volume of gas at standard conditions/hour/volume of catalyst. The water stream used for activation is preferably cobalt-free, but it may contain some free formic acid. A useful stream is the evaporator water overhead stream referred to in FIG. 1 which contains formic acid but has no cobalt. The time of treatment for regeneration is the time required to displace organic material from the pores.

FIG. 1 generally depicts a method for removing cobalt values from the crude product of a cobalt-catalyzed hydroformylation reaction formed from an olefinic feedstock having a carbon number in the range of $C_4$ to $C_{14}$, preferably $C_5$ to $C_7$. The crude product typically contains cobalt compounds in addition to an organic hydroformylation reaction product.

An olefin feedstock and syn gas are introduced into oxo reactor 1, wherein hydroformylation is conducted under conventional conditions to yield a crude hydroformylation product containing aldehydes, alcohols, by-products and cobalt catalyst compounds. This crude product is carried via conduit 3 where it is contacted with a stream of oxygen-containing gas, an organic acid and water, thereby producing a substantially cobalt-free organic hydroformylation reaction product and a water soluble cobaltous salt aqueous product, to settling drum or demetalling drum 5. In demetalling drum 5 the substantially cobalt-free crude product is separated from the water soluble cobaltous salt aqueous product. The substantially cobalt-free organic hydroformylation reaction product is diverted overhead via conduit 7 for further downstream treatment such as distillation or hydrogenation. The water soluble cobaltous salt aqueous product is carried via conduit 9 to evaporator 11 which concentrates the water soluble cobaltous salt, thereby producing a concentrated aqueous solution of cobaltous salt and a substantially cobalt-free water containing the organic acid, whereby the concentrated aqueous solution of cobaltous salt is separated from the substantially cobalt-free water containing the organic acid. The substantially cobalt-free water containing the organic acid is recycled via conduit 13 to oxo reactor 1. Whereas the concentrated aqueous solution of cobaltous salt is contacted with an alcohol stream and synthesis gas within conduit 15 before this mixture is passed to preformer reactor 17. In preformer reactor 17 the concentrated aqueous solution of cobaltous salt is converted to a cobalt carbonyl under catalytic conditions. The cobalt carbonyl from preformer reactor 17 is carried via conduit 19 to stripper reactor 21 where it is contacted with a stream of stripping gas at a temperature of not greater than 100° C. and at a pressure below 10.13 bar, the pressure of the cobalt compounds at the contacting temperature, to entrain volatile cobalt compounds in the stripping gas and to generate as bottoms alcohol products and dissolved cobaltous salts; whereby the entrained volatile cobalt compounds are taken out overhead via conduit 23 and the alcohol products and dissolved cobaltous salts are taken out as bottoms via conduit 25. The alcohol products are separated from the dissolved cobaltous salts in settling drum 27. The dissolved cobaltous salts are typically in an aqueous phase, e.g., an aqueous salt product, which can be readily separated from the organic phase, i.e., the alcohol products, by gravity settling. The alcohol products from settling drum 27 are preferably recycled to conduit 15 for mixing with the cobaltous salt upstream of preformer reactor 17 to act as a preformer solvent. The cobaltous salt from settling drum 27 is preferably recycled via conduit 29 to conduit 3 for further demetalling. Finally, the volatile cobalt compounds from conduit 23 are introduced into absorber 31 where they are contacted with olefinic feedstock, whereby the volatile cobalt compounds are absorbed into the olefinic feedstock and recycled to oxo reactor 1 via conduit 33. Reflux from absorber 31 is returned to stripper reactor 21 via reflux conduit 35. Optionally, syn gas may also be fed into stripper reactor 21 via reflux conduit 35.

Figure 2:
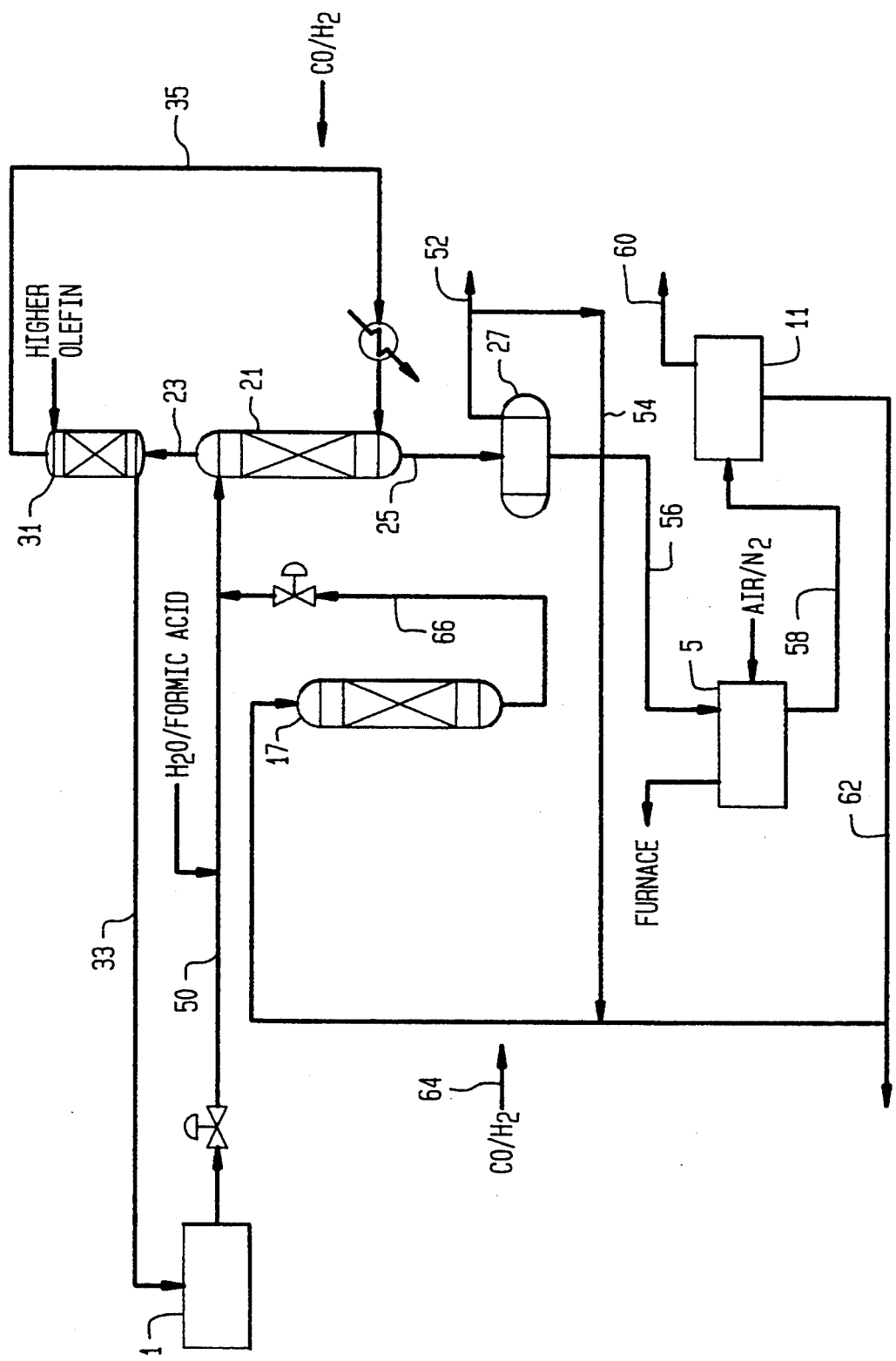
FIG. 2 illustrates an oxo process including a method for removing cobalt values wherein an acid-air cobalt demetalling step is disposed downstream of the stripping step in a Cobalt Flash process.

In FIG. 2 an olefin feedstock and syn gas which are introduced into an oxo reactor 1, wherein hydroformylation is conducted under conventional conditions to yield a crude hydroformylation product containing aldehydes, alcohols, by-products and cobalt catalyst compounds. This crude product is carried via conduit 50 where it is contacted with water and an organic acid, such as formic acid. The treated crude product is thereafter contacted with a stream of stripping gas in stripper reactor 21. The stripping typically occurs at a temperature of not greater than 100° C. and at a pressure below 10.13 bar, the pressure being lower than the decomposition pressure of the cobalt compounds at the contacting temperature, to entrain volatile cobalt compounds in the stripping gas, whereby the entrained volatile cobalt compounds are taken out overhead via conduit 23 and organic hydroformylation reaction products containing water soluble cobaltous salts dissolved therein are taken out as bottoms via conduit 25. The water soluble cobaltous salt is then separated from the organic hydroformylation reaction products by means of settling drum 27. The organic hydroformylation reaction product may be diverted from conduit 52 via conduit 54 and recycled to the preformer reactor 17. The water soluble cobaltous salt is carried via conduit 56 to settling drum or demetalling drum 5 where it is contacted with a stream of oxygen-containing gas, an organic acid and water thereby producing a water soluble cobaltous salt aqueous product. The oxygen should be present in an amount such that the organic acid only sees the water. Thereafter, the water soluble cobaltous salt aqueous product is carried via conduit 58 to evaporator 11 which forms a concentrated aqueous solution of cobaltous salt and a substantially cobalt-free water containing the organic acid. The concentrated aqueous solution of cobaltous salt is then separated from the substantially cobalt-free water containing the organic acid, whereby the substantially cobalt-free water containing the organic acid is recycled via conduit 60 to stripper reactor 21, diverted to the optional water wash treatment step, or diverted to hydrogenation. The concentrated aqueous solution of cobaltous salt is carried via conduit 62 either to preformer reactor 17 or recycled to oxo reactor 1. However, prior to being fed to preformer reactor 17, the concentrated cobaltous salt is contacted with an alcohol stream, a cobalt-free organic hydroformylation reaction product, or a hydrogenation product delivered via conduit 54 and syn gas which is delivered via conduit 64. This mixture is then passed to preformer reactor 17 where the concentrated aqueous solution of cobaltous salt is converted to a cobalt carbonyl. The cobalt carbonyl is then carried via conduits 66 and 50 to stripper reactor 21. Finally, the volatile cobalt compounds which are carried from stripper reactor 21 via conduit 23 are sent to absorber 31 wherein they are returned to oxo reactor 1 via conduit 33.

EXAMPLE 1

A 2% palladium on 2 mm carbon extrudate catalyst (sold by Engelhard Corporation) was charged to a batch autoclave reactor and contacted with an aqueous cobalt formate solution and a hydrocarbon in the presence of hydrogen and carbon monoxide at 4,000 psig (27.56 MPa) and 120° C.

Figure 3:
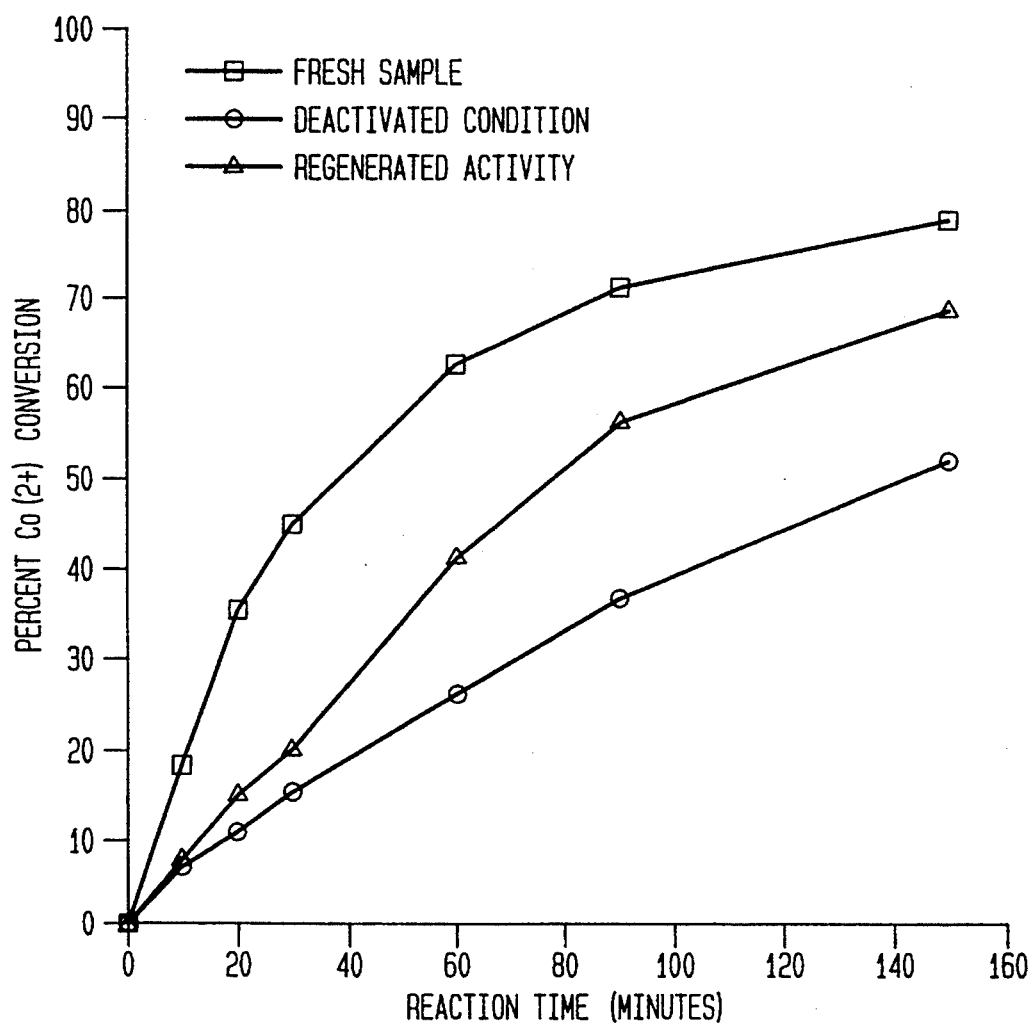
FIG. 3 is a graph comparing the catalytic activity of fresh catalyst, deactivated catalyst and regenerated catalyst from a batch reactor catalyst evaluation.

The percent conversion of Co(II) as a function of reaction time was measured and the results compiled in FIG. 3. The initial preforming catalytic activity of the fresh catalyst resulted in a conversion of 78.3% at the end of a 2.5 hour experiment. After a number of identical batch experiments with the same catalyst charge, the end-of-run conversion had declined to 51.6%. A reactivation wash was then conducted using one liter of 1.0 wt. % aqueous formic acid solution and one liter of hexyl alcohol at 160° C. and under syn gas pressure of 4,000 psig (27.56 MPa). The mixture was stirred at 2,500 rpm for two hours with a low syn gas off-flow allowed. After this wash, the next batch preforming experiment resulted in an end-of-run conversion of 68.3% which is an increase of 32.4% relative to the deactivated condition.

EXAMPLE 2

A 2% Pd on 1 mm carbon extrudate catalyst (sold by Johnson Matthey Corporation) was tested in a fixed bed continuous pilot plant reactor to convert an aqueous solution of cobalt formate to hydridocobalt carbonyl in the presence of an organic phase designated as $C_9$ oxo product which is composed nominally of 87 wt. % $C_9$ aldehyde, 5 wt. % $C_9$ alcohol and the remainder $C_8$ paraffin, $C_8$ olefin, and heavier materials. The aqueous solution of cobalt formate contained 0.9 wt. % cobalt. Nominal operating conditions were 1.0 LHSV, where LHSV is liquid hourly space velocity defined as volume feed/hour/volume of catalyst in the reactor, 1:1 volume ratio of aqueous cobalt formate solution to $C_9$ oxo product, 120° C. 3000 psig (20.67 MPa), 200% excess syn gas of 1:1 molar $H_2$:CO. After eight days of operation at these conditions, conversion of cobalt formate declined from 31% to 18%. At this time, a wash was carried out to reactivate the catalyst. The wash was conducted at 150° C. with syn gas of 1:1 molar $H_2$:CO and 1:1 volume ratio of hexyl alcohol to cobalt free water containing 1 wt. % formic acid. The combined flow rate of hexyl alcohol and cobalt free water resulted in a LHSV of 2.0 and the syn gas rate was 200 GHSV, where GHSV is gas hourly space velocity defined as volume of gas at standard conditions/hour/volume of catalyst in the reactor. The wash step was carried out for approximately sixteen hours. The catalyst was then tested at the original operating conditions with the same feed materials and the conversion of cobalt formate was measured to be 24%. This indicates a 33% improvement in cobalt formate conversion following the reactivation step.

What is claimed is:

1. A process for preparing oxo alcohols and aldehydes by the cobalt catalyzed hydroformylation of $C_2$ to $C_{17}$ linear or branched monoolefins with subsequent hydrogenation of the hydroformylation product, in which oxo process aqueous solutions of cobalt salts are converted to active hydrido cobalt carbonyl species in a preformet reactor, said preformer reactor containing a preformer metal catalyst being a metal of Group IB or VIII of the Periodic Table, or a non-metallic catalyst selected from the group consisting of activated carbon, ion exchange resins, silica alumina and zeolites, the improvement which comprises reactivating said preformer catalyst by treating it at a temperature of about 120° C. to 170° C. and a pressure of about 13.78 MPa to 31.00 MPa with a mixture of an aqueous organic acid solution and an alcohol for about 2 to 50 hours, whereby the conversion of said cobalt salts to said active cobalt catalyst species is improved when said salts are contacted with the treated preformer catalyst.

2. The process according to claim 1 wherein said preformer catalyst is a Group IB or VIII metal.

3. The process according to claim 2 wherein said metal is palladium.

4. The process according to claim 3 wherein said palladium is present as 2 wt. % palladium on an activated carbon support.

5. The process according to claim 1 wherein said aqueous organic salt solution comprises water and an organic acid.

6. The process according to claim 5 wherein said organic acid is at least one acid selected from the group consisting of: formic acid, acetic acid, propionic acid, and other acids having a boiling point approximately the same as water.

7. The process according to claim 5 wherein said organic acid is present in an amount between about 0.5 to 5.0 wt %, of free organic acid.

8. The process according to claim 1 wherein said an alcohol is at least one alcohol selected from the group consisting of: hexyl alcohols, heptyl alcohols, octyl alcohols, butanols and propanols.

* * * * *